United States Patent [19]

Ferrero et al.

[11] Patent Number: 5,476,827
[45] Date of Patent: Dec. 19, 1995

[54] PROCESS FOR THE SYNTHESIS OF ALDEHYDES AND THEIR DERIVATIVES AND CATALYST FOR USE THEREOF

[75] Inventors: Rose-Marie Ferrero, Lyons; Roland Jacquot, Sainte Foy les Lyon, both of France

[73] Assignee: Rhone-Poulenc Chimie, Courbevoie Cedex, France

[21] Appl. No.: 220,171

[22] Filed: Mar. 30, 1994

Related U.S. Application Data

[62] Division of Ser. No. 966,385, Oct. 26, 1992, Pat. No. 5,334,769.

[30] Foreign Application Priority Data

Oct. 24, 1991 [FR] France ................... 91 13147

[51] Int. Cl.[6] .................... B01J 23/14; B01J 23/46
[52] U.S. Cl. ............... 502/227; 502/230; 502/332; 502/352
[58] Field of Search ............... 568/484, 435; 502/227, 229, 325, 352

[56] References Cited

U.S. PATENT DOCUMENTS

| | | |
|---|---|---|
| 3,691,102 | 9/1972 | Swift ..................... 502/325 |
| 3,935,265 | 1/1976 | Fienstein et al. . |
| 4,328,373 | 5/1982 | Strojny . |
| 4,356,328 | 10/1982 | Moy . |
| 4,522,935 | 6/1985 | Robinson et al. ............... 502/227 |
| 4,585,900 | 4/1986 | Holy et al. . |
| 4,613,700 | 9/1986 | Maki et al. . |
| 4,677,094 | 6/1987 | Moser et al. ............... 502/230 |
| 5,334,769 | 8/1994 | Ferrero et al. ............... 568/435 |

OTHER PUBLICATIONS

Journal of Catalysis, vol. 121, pp. 174–182, "Studies of Ruthenium–Tin Boride Catalysts", by V. M. Desphande et al, Jan. 1990, Duluth, Minn. US.

Journal of Catalysis, vol. 114, No. 11, 18 Mar. 1991, Columbus, Ohio, abstract No. 101124W, p. 668, col. 1 & IN–A–165539–Apr. 11, 1989 (I.E.L. Ltd.).

*Primary Examiner*—Anthony McFarlane
*Attorney, Agent, or Firm*—Burns, Doane, Swecker & Mathis

[57] ABSTRACT

A process for the preparation of aldehydes by hydrogen reduction of carboxylic acids, esters or anhydrides, characterized in that the reduction conducted in the vapor phase, in the presence of a bimetallic catalyst of the ruthenium/tin type.

13 Claims, No Drawings

PROCESS FOR THE SYNTHESIS OF ALDEHYDES AND THEIR DERIVATIVES AND CATALYST FOR USE THEREOF

This application is a divisional of application Ser. No. 07/966,835, filed Oct. 26, 1992, now U.S. Pat. No. 5,334,769.

The present invention relates to a process for the synthesis of aldehydes and their derivatives. It more particularly relates to a process for the synthesis of aldehydes by vapour reduction of acids, esters or their derivatives.

It is known from the prior art to prepare saturated aliphatic or aromatic aldehydes by the reduction of the corresponding esters or acids by means of a catalyst chosen from among cerium, zirconium, uranium, praseodymium and yttrium oxides at a temperature between 350° and 450° C. (U.S. Pat. No. 4,328,373).

It is also known to prepare aromatic aldehydes by the reduction of the corresponding acids or esters in the presence of a zirconium oxide-based catalyst containing an additive chosen from among e.g. chromium, manganese, iron, cobalt or zinc, or from among certain elements of group III of the periodic classification of elements such as aluminium, scandium, yttrium or gadolinium (EP 150 961). This process is performed at temperatures above 300° C.

Bearing in mind temperature conditions required for their performance, these processes do not make it possible to prepare aldehydes from thermosensitive acids such as phenol acids. In addition, these processes do not make it possible to prepare unsaturated aldehydes from unsaturated acids.

The present invention aims at obviating these disadvantages. The Applicant has in fact demonstrated that bimetallic ruthenium-tin catalysts make it possible to hydrogenate acids at lower temperatures, so that it is possible to reduce thermosensitive acids into aldehydes, selectively reduce unsaturated esters or acids into unsaturated aldehydes or prepare with high yields aldehydes from saturated aliphatic or aromatic acids.

Therefore one object of the invention is a process for the preparation of aldehydes by the reduction of carboxylic anhydrides, esters or acids, characterized in that the process is conducted in the vapour phase, in the presence of a bimetallic ruthenium-tin catalyst.

In the following description of the invention, the term bimetallic ruthenium-tin catalyst is understood to mean a catalyst incorporating as active elements at least ruthenium and tin.

Catalysts of the Ru/Sn/B type have already been described in the literature [J. Cat., 121, 165–173 (1990)], together with their use for the liquid phase reduction of unsaturated fatty acids into unsaturated fatty alcohols [J. Cat., 121, 174–182 (1990)]. However, the above documents do not suggest the possibility of using bimetallic catalysts of the ruthenium-tin type for the preparation of aldehydes from acids.

The invention is more particularly directed at the preparation of aldehydes of general formula:

$$R-\underset{H}{\overset{\displaystyle C=O}{|}} \qquad (I)$$

in which R represents a hydrogen atom or a hydrocarbon radical, which may be substituted, having 1 to 40 carbon atoms and which can be a straight or branched-chain, saturated or unsaturated, acyclic aliphatic radical, a monocyclic or polycyclic, saturated, unsaturated or aromatic carbocyclic or heterocyclic radical by the reduction of esters, anhydrides or acids of formula:

$$R-\underset{O-R'}{\overset{\displaystyle C=O}{|}} \qquad (II)$$

in which:
R is as defined hereinbefore,
R' represents:
an R grouping as defined hereinbefore,
a $$R''-\underset{|}{\overset{\displaystyle C=O}{|}}$$

grouping, in which R" has the meaning given for R, it being possible to link together the two groupings R and R" for forming a saturated or unsaturated ring having 5 to 7 atoms and incorporating the anhydride function,
by means for two neighboring atoms, the two grouping R and R" can together form a bridge of an ortho-condensed bicyclic system.

The carboxylic acids or derivatives used preferably comply with formula (II), in which R represents an optionally substituted hydrocarbon radical having 1 to 20 carbon atoms.

The process according to the invention is applicable to any monocarboxylic or polycarboxylic acid such as saturated or unsaturated aliphatic acids; carboxylic or heterocyclic, saturated, unsaturated or aromatic, monocyclic or polycyclic; saturated or unsaturated aliphatic carrying a cyclic substituent such as a saturated, unsaturated or aromatic heterocyclic or carbocyclic ring.

It is particularly suitable for the preparation of aldehydes from unsaturated or saturated, aliphatic carboxylic acids such as fluoral and in particular those having a conjugate double bond with the carbonyl group of the carboxylic, ester or anhydride function.

It is highly suitable for the synthesis of aldehydes from aromatic carboxylic acids, particularly benzoic acids, more particularly hydroxybenzoic and halobenzoic acids, preferably fluorobenzoic acids.

In the following description of the invention the term aromatic is understood to mean the conventional notion of aromaticity such as is defined in the literature by Jerry March, Advanced Organic Chemistry, 3rd edition, John Wiley and Sons, 1985, p. 37 ff. The term benzoic acid is understood to mean any aromatic compound carrying at least one COOH function.

According to the process of the invention, it is possible to use any random carboxylic acid which will be in gaseous form under the conditions of the invention.

Thus, the starting material can be constituted by a carboxylic acid complying with formula (II), in which the residue R represents a substituted or unsubstituted, hydrocarbon radical, which can be an aliphatic, acyclic, saturated or unsaturated, branched or straight-chain radical, a monocyclic or polycyclic, saturated, unsaturated or aromatic heterocyclic or carbocyclic radical.

Particularly suitable for performing the process of the invention are carboxylic acids of general formula (II), in which R represents an optionally substituted, monocyclic or polycyclic, aromatic hydrocarbon residue.

Any random substituent can be present on the ring, provided that it does not disturb the reduction reaction of the carboxylic function.

R preferably represents an aromatic and particularly benzene, hydrocarbon radical complying with the general formula (III):

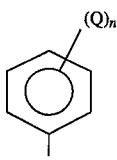
(III)

in which:
n is an integer from 0 to 5 and preferably 0 to 3. O represents $R_1$, $R_1$ being one of the following groups or functions:
a straight or branched-chain radical with 1 to 6 carbon atoms and preferably 1 to 4 carbon atoms, such as methyl, ethyl, propyl, isopropyl, butyl, isobutyl, sec.-butyl or tert.-butyl;
a straight or branched-chain alkenyl radical having 2 to 6 carbon atoms and preferably 2 to 4 carbon atoms, such as vinyl or allyl;
a straight or branched-chain alkoxy radical having 1 to 6 carbon atoms, preferably 1 to 4 carbon atoms such as methoxy, ethoxy, propoxy, isopropoxy or butoxy radicals;
an acyl group having 2 to 6 carbon atoms;
a radical of formula:

$-R_2-OH$ $-R_2-COOR_5$ $-R_2-CHO$ $-R_2-NO_2$ $-R_2-CN$ $-R_2-(NR_5)_2$ $-R_2-CO-(NR_5)_2$ $-R_2-SH$ $-R_2-X$ $-R_2-CF_3$ in which $R_2$ represents a valency bond or a straight or branched-chain, saturated or unsaturated, divalent hydrocarbon radical having 1 to 6 carbon atoms such as e.g. methylene, ethylene, propylene, isopropylene or isopropylidene; $R_5$ represents a hydrogen atom or a straight or branched-chain alkyl radical with 1 to 6 carbon atoms; X symbolizes a halogen atom, preferably a chlorine, bromine or fluorine atom.
Q represents $R_3$, $R_3$ being one of the more complex radicals given hereinafter:
a radical

in which $R_1$ and $R_2$ have the meanings given hereinbefore and m is an integer from 0 to 5, preferably 0 to 3; or a radical $-R_2-A-R_4$, in which $R_2$ has the meaning given hereinbefore, $R_4$ represents a straight or branched-chain alkyl radical with 1 to 6 and preferably 1 to 4 carbon atoms or a radical of formula

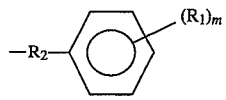

where A symbolizes one of the following groups:

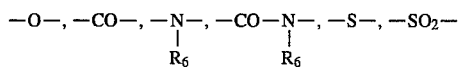

in which $R_6$ represents a hydrogen atom or a straight or branched alkyl radical with 1 to 4 carbon atoms and preferably a methyl or ethyl radical.
When n exceeds 1, the radicals Q can be the same or different and two successive carbon atoms of the benzene ring can be interconnected by a ketal bridge such as extranuclear methylene dioxy or ethylene dioxy radicals. Preferably n is equal to 0, 1, 2 or 3.
Among the aforementioned residues R, preference is given within the process of the invention to the use of carboxylic acids or derivatives complying with the general formula (II), in which R represents an aromatic residue complying with the general formula (III) in which: n is equal to 0, 1, 2 or 3; Q represents one of the following groups or functions:
a hydrogen atom,
a straight or branched-chain alkyl radical with 1 to 4 carbon atoms,
a straight or branched-chain alkoxy radical with 1 to 4 carbon atoms,
a methylene or ethylene dioxy radical,
a —OH group,
a —CHO group,
a $NH_2$ group,
a phenyl radical,
a halogen atom,
or a $CF_3$ group.
In even more preferred manner a choice is made of compounds of formula (II) in which the radicals Q, which can be the same or different are a hydrogen atom, a hydroxyl group, a methyl radical, a methoxy radical or a —CHO group.
As examples or radicals R complying with formula (III), more specific reference can be made to the phenyl, tolyl or xylyl radicals and the biphenyl, 1,1'-methylene biphenyl, 1,1'-isopropylidene biphenyl, 1,1'-oxybiphenyl, 1,1'-imino biphenyl radicals and these radicals can be substituted by one or more radicals Q as defined hereinbefore and preferably a hydroxyl group or a halogen atom.
R can also have a polycyclic aromatic hydrocarbon residue. Together the rings can form ortho-condensed and ortho and peri-condensed systems. More particular reference is made to a naphthalene residue. The said rings can be substituted by 1 to 4 $R_1$ radicals and preferably 1 to 3 $R_1$ radicals having the meanings given hereinbefore for the substituents of the aromatic hydrocarbon residue of general formula (III).
In general formula (II) of the carboxylic acids, R can also represent a saturated carbocyclic residue or a carbocyclic residue which has 1 or 2 unsaturations in the ring, generally having 3 to 7 and preferably 6 carbon atoms in the ring, whereby said ring can be substituted by 1 to 5 and preferably 1 to 3 $R_1$ radicals having the meanings given hereinbefore for substituents of the aromatic hydrocarbon residue of general formula (III).

Preferred examples of R radicals are cyclohexyl or cyclohexenyl, radicals, optionally substituted by straight or branched-chain alkyl radicals having 1 to 4 carbon atoms. As stated hereinbefore, R can represent a straight or branched-chain, saturated or unsaturated, acyclic aliphatic residue.

More preferably, R represents a straight or branched-chain, acyclic aliphatic residue having preferably 1 to 12 carbon atoms, which is saturated or has one or more unsaturations on the chain and in general 1 to 3 unsaturations, which can be single or conjugate double bonds or triple bonds.

The hydrocarbon chain can optionally be:
interrupted by one of the following groups:

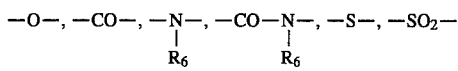

in which $R_6$ represents hydrogen or a straight or branched-chain alkyl radical with 1 to 4 carbon atoms, preferably a methyl or ethyl radical,
and/or carry one of the following substituents:
—OH, —COOR$_5$, —CHO, —NO$_2$, —CN, —NH$_2$, —SH, —X, —CF$_3$,
in which $R_5$ has the meaning given hereinbefore.

In a preferred embodiment of the invention, R complies with the following formula:

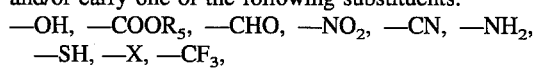

(IV)

in which $R_7$, $R_8$ and $R_9$, which can be the same or different, are chosen from among a hydrogen atom, a straight or branched-chain alkyl radical containing 1 to 10 carbon atoms, a straight or branched-chain alkenyl radical containing 1 to 10 carbon atoms, a straight or branched-chain alkoxy radical containing 1 to 10 carbon atoms, a hydroxyl group, an amine function or a halogen or a —CF$_3$ group. Preferably, $R_7$ and/or $R_8$ and/or $R_9$ represent an unsaturated grouping.

In even more preferred manner, in formula (IV), one of the three groupings, $R_7$, $R_8$ and $R_9$ has a conjugate double bond with the carbonyl grouping of the carboxylic anhydride, ester or acid.

It is also possible to make use of a carboxylic acid or derivative of formula (II), in which R represents a straight or branched-chain saturated or unsaturated, acyclic aliphatic residue, which can optionally carry a cyclic substituent. For example, it is an aromatic, saturated or unsaturated carbocyclic or heterocyclic ring.

The acyclic aliphatic residue can be bonded to the ring by a valency bond or by one of the following groups:

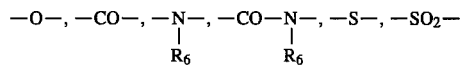

in which $R_6$ has the meaning given hereinbefore.

As examples of cyclic substituents, it is possible to use cycloaliphatic, aromatic or heterocyclic substituents, particularly cycloaliphatic substituents having 6 carbon atoms in the cycle or benzene substituents, said cyclic substituents being themselves optionally carriers of 1, 2, 3, 4 or 5, identical or different $R_1$ radicals, in which $R_1$ has the meanings given hereinbefore for the substituents of the aromatic hydrocarbon residue of general formula (III). As examples of such radicals, mention can inter alia be made of the benzyl radical.

In the general formula (II) of the carboxylic acids, R can also represent a saturated or unsaturated, heterocyclic residue having in particular 5 or 6 atoms in the ring, including 1 or 2 heteroatoms such as nitrogen, sulphur and oxygen atoms. The carbon atoms of the heterocycle can optionally be substituted wholly or partly by $R_1$ radicals, $R_1$ having the meanings given hereinbefore for the substituents of the aromatic hydrocarbon residue of the general formula (III).

R can also represent a polycyclic heterocyclic residue defined as being either a radical constituted by at least two aromatic or non-aromatic heterocycles containing at least one heteroatom in each ring and forming together ortho or ortho and peri-condensed systems or a radical constituted by at least one aromatic or non-aromatic hydrocarbon ring and at least one aromatic or non-aromatic heterocycle forming together ortho or ortho and peri-condensed systems. The carbon atoms of said rings can optionally be wholly or partly substituted with respect to part of them only by $R_1$ radicals, $R_1$ having the meanings given hereinbefore for the substituents of the aromatic hydrocarbon residue of general formula (III).

As examples of R groupings of the heterocyclic type, inter alia reference can be made to furyl, pyrrolyl, thienyl, isoxazolyl, furazanyl, isothiazolyl, imidazolyl, pyrazolyl, pyridyl, pyridazinyl, pyrimidinyl, quinolyl, naphthyridinyl, benzofuranyl and indolyl radicals.

As carboxylic acids having at least one carboxylic group complying with formula (II), use can in particular be made of the following carboxylic acids:

saturated, aliphatic, monocarboxylic acids such as formic, acetic, propionic, butyric, isobutyric, valeric, isovaleric, pivalic, lauric, myristic, palmitic and stearic acids;

saturated, aliphatic, dicarboxylic acids such as oxalic, malonic, succinic, glutaric, adipic, pimelic, suberic, azelaic and sebacic acids;

unsaturated, aliphatic, monocarboxylic acid or dicarboxylic acids such as acrylic, propiolic, methacrylic, crotonic, isocrotonic, senecioic, tiglic, oleic, maleic, fumaric, citraconic and mesaconic acids;

saturated or unsaturated, carbocyclic, carboxylic acids such as camphoric or chrysanthemic acids;

heterocyclic, carboxylic acids such as furan carboxylic, thiophene, carboxylic, pyrrole carboxylic, pyrazine carboxylic, nicotinic, isonicotinic and picolinic acids;

aromatic, carbocyclic, carboxylic acids such as benzoic, phthalic, isophthalic, terephthalic, naphthalene carboxylic & toluic acids;

saturated, aryl aliphatic, carboxylic acids such as in particular arylpropionic acids, such as 2-phenyl propionic, 4-[(2-butyl)- 2-phenyl]-propionic, (3-benzoyl phenyl)-2-propionic, (6-methoxy- 2-naphthyl)-2-propionic acids or unsaturated acids such as e.g. 2-phenyl-propenoic and cinnamic acids;

halogenated aliphatic or aromatic, carboxylic acids such as monofluoroacetic, difluoroacetic, monochcloroacetic, dichloroacetic, trichloroacetic, monochloropropionic, α-bromopropionic, α-bromobutyric, trifluoroacetic, monofluoro-o-benzoic, monofluoro-m-benzoic, monofluoro-p-benzoic, difluoro-2,3-benzoic, difluoro-2,4-benzoic, difluoro-2,5-benzoic, difluoro-3,4-benzoic, trifluoro-2,3,6-benzoic, trifluoro-2,4,5-benzoic, tetrafluoro- 2,3,5-benzoic, pentafluorobenzoic, α,α,α-trifluoro-o-toluic, α,α,α-trifluoro-m-toluic, α,α,α-trifluoro-p-toluic, monochloro-o-benzoic, monochloro-m-benzoic, monochloro-p-benzoic dichloro- 2,3-benzoic, dichloro-2,4-benzoic, dichloro-2,5-benzoic, dichloro-2,6-benzoic, dichloro-3,4-benzoic, dichloro-3,5-benzoic, trichloro-2,3,5-benzoic, trichloro-2,3,6-benzoic, 2-chloro-4,5-fluorobenzoic, 3-chloro-2,4,5-trifluorobenzoic, monobromo-o-benzoic, monobromo-m-benzoic and monobromo-p-benzoic acids;

aliphatic, cycloaliphatic and aryl aliphatic hydroxy acids such as glycolic, lactic, glyceric, 2-hydroxy butanoic, 3-hydroxy butanoic, 2-methyl lactic, 2-hydroxy-4-methyl thiobutanoic, tartronic, malic, tartric, 1-hydroxycyclopropane carboxylic, 2-hydroxyphenylpropanoic, 2-hydroxycinnamic, 3-hydroxycinnamic and 4-hydroxycinnamic acids;

the following hydroxy benzoic acids: 2-hydroxy benzoic (salicyclic acid), 3-hydroxy benzoic, 4-hydroxy benzoic, 3-methyl salicylic, 4-methyl salicyclic, 5-methyl salicyclic, 3-hydroxy-4-methyl benzoic, 3-methoxysalicylic, 4-methoxysalicylic, 5-methoxysalicylic, 3-hydroxy-4-methoxybenzoic (isovanillic acid), 4-hydroxy-3methoxybenzoic (vanillic acid), 3-hydroxy-4,5-dimethoxybenzoic, 4-hydroxy-3,5-dimethoxybenzoic (syringic acid), 5-hydroxy isophthalic, 3-aminosalicyclic, 4-aminosalicylic, 5-aminosalicylic, 3-hydroxy-2-amino benzoic, 3-nitrosalicylic, 3-hydroxy-4-nitrobenzoic, 4-hydroxy-3-nitrobenzoic, 3-hydroxy- 4-methyl-2-nitrobenzoic, 3,5-diiodosalicylic, 2,3-dihydroxy benzoic, 2,4-dihydroxy benzoic, 2,5-dihydroxy benzoic, 2,6-dihydroxy benzoic, 3,4-dihydroxy benzoic (protocatechuic acid), 3,5-dihydroxy benzoic, 3,5-dihydroxy-4-methyl benzoic, 2,3,4-trihydroxy benzoic, 2,4,6-trihydroxy benzoic and 3,4,5-trihydroxy benzoic acids;

alkoxy and phenoxy acids such as methoxyacetic, phenoxyacetic, 2,4-dichloro phenoxyacetic, phenoxypropionic, 2,4-dichloro phenoxypropionic, p-hydroxyphenoxypropionic, m-chlorophenoxypropionic, 4-phenoxybenzoic, (4-carboxy-4-phenoxy)-benzoic and piperonylic acids, oxo acids such as 2-acetyl benzoic, 4-acetyl benzoic, 2-benzoyl benzoic and 4-benzoyl benzoic acids;

acyloxy acids such as 3-benzoyloxypropionic, 2-acetoxy benzoic and 4-acetoxy benzoic acids;

amido acids such as 2-acetamido acrylic, 2-acetamido benzoic, 3-acetamido benzoic and N-4-acetamido benzoic acids;

amino acids optionally N-protected by a protective group such as e.g. the following groups acyl (acetyl, benzoyl), BOC (butyloxycarbonyl), CBZ (carbobenzoxy), FMOC (9-fluoroenyl-methoxycarbonyl) and MSOC (2-methanesulphenyl-ethoxycarbonyl).

Reference can be made to the following amino acids:

aliphatic amino acids: glycine, alanine, valine, leucine and isoleucine, hydroxylated amino acids: serine and threonine;

sulphurized amino acids: cysteine and methionine;

dicarboxylic amino acids and their amides: aspartic acid, asparagine, glutamic acid and glutamine;

amino acids having two basic groupings: lysine, argine and histidine;

aromatic amino acids: phenylalanine, tyrosine and tryptophane; imino acids: proline and hydroxyproline.

Among all the compounds given hereinbefore for illustration purposes and without limitation, the process according to the invention is more particularly advantageously applicable to the following compounds:

salicylic and 4-hydroxybenzoic acids;

acetic and propionic acids and their derivatives substituted by a hydroxy, halogen, phenyl or phenyloxy group;

benzoic acid and its derivatives substituted by an alkyl $C_1$–$C_4$ group, acetoxy, acetamido, hydroxy, methoxy and ethoxy;

halogenated aliphatic or aromatic, carboxylic acids such as monofluoroacetic, difluoroacetic, monochloroacetic, dichloroacetic, trichloroacetic, monochloropropionic, α-bromopropionic, α-bromobutyric, trifluoroacetic, monofluoro-o-benzoic, monofluoro-m-benzoic, monofluoro-p-benzoic, difluoro-2,3-benzoic, difluoro-2,4-benzoic, difluoro-2,5-benzoic, difluoro-3,4-benzoic, trifluoro-2,3,6-benzoic, trifluoro-2,4,5-benzoic, tetrafluoro- 2,3,5-benzoic, pentafluorobenzoic, α,α,α-trifluoro-o-toluic, α,α,α-trifluoro-m-toluic, α,α,α-trifluoro-p-toluic, monochloro-o-benzoic, monochloro-m-benzoic, monochloro-p-benzoic, dichloro- 2,3-benzoic, dichloro-2,4-benzoic, dichloro-2,5-benzoic, dichloro-2,6-benzoic, dichloro-3,4-benzoic, dichloro-3,5-benzoic, trichloro-2,3,5-benzoic, trichloro-2,3,6-benzoic, 2-chloro-4,5-fluorobenzoic, 3-chloro-2,4,5-trifluorobenzoic, monobromo-o-benzoic, monobromo-m-benzoic and monobromo-p-benzoic acids, nicotinic acid.

As stated hereinbefore, it is also possible to use carboxylic acid defined hereinbefore in the form of its ester. In this case in formula (II), R' preferably represents an aliphatic radical containing 1 to 10 carbon atoms, optionally in substituted form. More preferably, R' represents a straight or branched-chain alkyl radical with 1 to 6 carbon atoms. As examples of preferred R' radicals, reference can be made to methyl, ethyl or hexyl radicals. The preferred esters are those derived from the list of the aforementioned carboxylic acids.

According to the present invention, it is possible to use a carboxylic acid in the form of its anhydride. As examples of carboxylic anhydrides, reference can more particularly be made to anhydrides of the aforementioned carboxylic acids and cyclic anhydrides.

Thus, when the anhydride complies with formula (II), in which R' is a

grouping, the two groupings R and R' can be interlinked to form a saturated or unsaturated ring having 5 to 7 atoms incorporating the anhydride function. They preferably form a straight or branched-chain alkylene radical with 2 to 6 carbon atoms or in even more preferred manner a —$(CH_2)_t$— radical with t equal to 2 to 4.

Examples of cyclic anhydrides are succinic anhydride or maleic anhydride.

When the anhydride complies with formula (II) in which R' is a

grouping, the two groupings R and R", by means of two neighboring atoms, can together form a bridge of an ortho-condensed bicyclic system.

The preferred compounds are bicyclic and constituted by a benzene ring and a heterocycle, because the ring comprises the oxygen atom of the anhydride function, said ring preferably having 5 to 6 atoms. As examples of such cyclic anhydrides of polycarboxylic acids references can be made to phthalic anhydride.

The process according to the invention is carried out in the gaseous phase. Advantageously, the reaction is performed at a temperature between 100° to 500° C. and in even more preferred manner between 200° and 400° C. It is understood that the temperature can be adapted by the Expert as a function of the starting acid and the sought reaction speed.

Moreover, it can be particularly advantageous to perform a prior activation of the catalyst by a pronounced temperature rise. In particular, the catalyst can previously be exposed in temperatures close to approximately 500° C. and preferably 450° C. Activation advantageously takes place under a hydrogen stream.

A practical way of performing the present invention consists of introducing into a reactor a desired catalyst quantity, optionally between two quartz bends in order to aid the contacting of the reagents. The reactor temperature is then raised under a hydrogen stream to a given value making it possible to activate the catalyst and is then restored to the reaction temperature. The acid is then injected at the desired flow rate and the aldehyde formed is recovered. Preferably, the acid is injected directly in gaseous form after having been vaporized by heating.

However, it can also be injected in solution in an inert solvent for the reaction. As inert solvents reference can in particular be made to aliphatic hydrocarbons (e.g. hexane), alicyclic hydrocarbons (e.g. cyclohexane), aromatic hydrocarbons (e.g. toluene) or ethers (e.g. dimethoxyethane).

Under the effect of the high temperature, the thus injected acid is vaporized at the first quartz bed. The hydrogen can be injected under atmospheric pressure or a low pressure compatible with the vapour phase (a few bars, e.g. 0.5 to 10 bars). The hydrogen can also be diluted in an inert gas such as nitrogen or helium.

Advantageously, for 1 ml of catalyst, the hydrogen is injected at a flow rate between 0.1 and 10 liters per hour and the acid at a liquid flow rate at the most equal to 10 ml/h and preferably between 0.5 and 5 ml/h.

At the end of the reaction, the aldehyde is recovered by any appropriate means such as distillation or crystallization. In certain cases, particularly in the case of fluoral, the aldehyde can be obtained in a hydrated form.

Different types of catalyst can be used in the present invention and in particular the catalyst may or may not be supported.

More generally, the ruthenium represents between 0.1 and 50% by weight of the catalyst. In the case where use is made of a mass catalyst, the ruthenium represents 10 to 50% by weight of the catalyst.

In a preferred embodiment, use is made of a supported catalyst. To this end the support can be chosen from among oxides of metals, such as oxides of aluminium, silcon and/or zirconium, or from among carbons, optionally activated by a known treatment using nitric acid, acetylene black or resins. It is generally preferable to choose a support not having an excessively high specific surface, in order to limit the risks of direct interaction between the support and the reagents.

In the case of a supported catalyst, the ruthenium content is adapted by the Expert as a function of the support (nature and specific surface) and the sought reaction speed.

Generally, the catalyst ruthenium content is advantageously chosen between 0.1 and 20.0% by weight and in even more preferred manner between 0.5 and 3.0% by weight.

In exemplified manner only, it is pointed out that the specific surface (B.E.T.) of the support is advantageously chosen between 50 and 100 $m^2/g$, when the catalyst ruthenium content is between 0.1 and 1%.

Advantageously, the invention makes use of catalysts in which the tin (Sn)/ruthenium (Ru) molar ratio is between 1 and 10 inclusive and even more preferably between 2 and 6 inclusive.

A first embodiment of the invention makes use of a ruthenium-tin-boron catalyst. In this case, the boron content is generally below 1% and most frequently close to 0.5%.

The catalysts usable in the process according to the invention can be prepared in different ways and in particular by impregnation according to the process described by Desphande et al. [J. Cat., 121, 165–173 (1900)], which is incorporated herein by reference.

Generally, dissolving takes place in water of the two metals in the form of salts, optionally in the presence of the support and impregnation is allowed to take place over approximately 15 hours. As a function of the particular case, it is then possible to add a chemical reducing agent before recovering and washing the bimetallic catalyst, which is then dried in air, prior to its use. Among the usable chemical reducing agents, reference can in particular be made to borohydrides, such as sodium, lithium, potassium or tetrabutylammonium borohydrides, as well as hydrazine or formol. According to another preferred embodiment of the process according to the invention use is made of a novel bimetallic catalyst incorporating ruthenium and tin, but which is free from boron, the active elements preferably being supported. In order to prepare it it is possible to use per se known methods for the preparation of supported metal catalysts.

One of the said preparation processes e.g. consists of introducing a support into a solution, which is prepared by dissolving at least one appropriate compound of the chosen elements. The deposition of the active elements on the support is carried out by distilling the solvent, preferably water, which can be eliminated by evaporation under reduced pressure preferably chosen between 5 and 20 mm of mercury. The thus obtained contact mass undergoes a reduction by means of a hydrogen stream.

According to another conventional preparation procedure, the deposition of the compound or compounds supplying the metallic elements on the support is carried out by precipitating the compounds in per se known manner and subjecting the thus obtained contact mass to reduction by means of hydrogen.

The deposition on the support of several metallic elements can obviously by carried out successively, but is preferably performed simultaneously.

The nature of the compounds supplying the metallic elements used for the preparation of the catalysts according to the invention is not critical. It is possible to use the metals themselves, such as ruthenium and tin.

As examples of compounds which can be used for the preparation of the catalysts according to the invention, reference can be made to compounds of ruthenium, ruthenium (III) chloride, ruthenium (IV) chloride, ruthenium pentafluoride, ruthenium (II) oxide, ruthenium (IV) oxide, ammoniacal ruthenium oxychloride, $Ru_2(OH)_2Cl_4 7NH_3 5H_2O$ ruthenium acetate and, as compounds of tin, tin oxides, chlorides, nitrates, carboxylates and alkoxides, or metalorganic compounds in which the tin is linked with a hydrogen atom and/or alkyl radicals preferably having 1 to 4 carbon atoms. The preferred salts are compounds of ruthenium such as ruthenium (III) chloride, compounds of tin such as tin (II) chloride, tin (IV) chloride, tin (II) acetate, tin (II) octoate and tin ethyl hexanoate.

Therefore another object of the invention is a bimetallic catalyst constituted by tin and ruthenium in a molar ratio from 1 to 10 and optionally on a support. In the preferred catalysts, the molar ratio is chosen between 4 and 6.

The present invention is particularly suitable for the preparation of aromatic aldehydes and particularly the aldehydes complying with the formula:

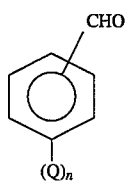

(V)

in which:
n is equal to 0, 1, 2 or 3,
Q represents one of the following groups or functions:
  a hydrogen atom,
  a straight or branched-chain alkyl radical with 1 to 4 carbon atoms,
  a straight or branched-chain alkoxy radical with 1 to 4 carbon atoms,
  a methylene or ethylene dioxy radical,
  a —OH group,
  a —CHO group,
  a $NH_2$ group,
  a phenyl radical,
  a halogen atom,
  or a $CF_3$ group.

The invention makes is possible to prepare numerous aldehydes, which are used as pharmaceutical and/or agrochemical intermediates, such as e.g. 3,4-difluorobenzaldehyde and 4-chlorobenzaldehyde.

It is particularly interesting for the preparation of salicyclic aldehyde, which can inter alia be used for the preparation of coumarin. The salicylic aldehyde obtained according to the process of the invention can be used as a starting materials in the synthesis of coumarin. The latter results from a well known cyclization state, which is adequately described in the literature. Reference can in particular be made to the preparation of coumarin according to the Perkin reaction by reacting salicylic aldehyde and acetic anhydride in the presence of sodium acetate (KIRK-OTHMER—Encyclopedia of Chemical Technology 7, p. 198, 3rd edition) which is corporated herein by reference.

The process according to the invention is also suitable for the preparation of other aromatic aldehydes such as 3-hydroxy benzeldehyde, 4-hydroxy benzaldehyde, vanillin, veratraldehyde, p-anisaldehyde and piperonal.

The present invention is also usable for the synthesis of various aldehydes. It can be used for the preparation of saturated aldehydes such as fluoral or acetaldehyde. It is particularly suitable for the synthesis of unsaturated aldehydes, particularly in the chemistry of terpenes (prenal, citral, etc.), synthesis intermediates of vitamins A or E.

The invention is particularly suitable for the preparation of aldehydes of formula:

(VI)

in which $R_{10}$ and $R_{11}$, which can be the same or different, are chosen from among alkyl radicals having approximately 1 to 20 carbon atoms and phenyl and naphthyl radicals optionally substituted by alkyl radicals having 1 to 20 carbon atoms. As an example of aldehydes reference can be made to prenal and cinnamaldehyde.

It does not fall outside the scope of the present invention if the process according to the invention is used to produce aldehydes in the form of their derivatives such as their acetals or their hemiacetals, by reacting the aldehyde and an alcohol which is introduced either together with the acid or at the end of the reaction. Examples of alcohols which are used conventionally are methanol or ethanol.

The following examples are given in a purely illustrative and non-limitative manner.

EXAMPLE 1

In a 1 liter three-necked flask are introduced 0.37 g of $RuCl_3$, $xH_2O$ with x equal to approximately 2 (dissolved beforehand in 40 ml of water). Accompanies by stirring and in 30 minutes, addition takes place of 1.5 g of $SnCl_2$, $2H_2O$ dissolved in 120 ml of water. Accompanied by stirring, addition then takes place of 25 g of γ-alumina. Stirring takes place for 15 minutes. Stirring is stopped and the produce is left to rest for 16 hours, at the end of which 25 ml of water are added, accompanies by stirring.

5.5 g of $NaBH_4$ are dissolved in 500 ml of water, which is added dropwise and at ambient temperature to the catalyst. Reduction takes place for 1 hour accompanies by stirring and for 16 hours without stirring. Once the reduction has taken place, the catalyst is filtered, then washed 5 times with 500 ml of water and once with 500 ml of ethanol.

The catalyst is then dried at ambient temperature, which gives a Ru-Sn-B/γAl$_2$O$_3$ catalyst with Sn/Ru=4.7 (mole/mole), i.e. 1.2% Ru (wt/wt) and 3% Sn (wt/wt).

EXAMPLE 2

Into a diameter 18 mm tubular glass reactor is introduced 1 ml of the catalyst obtained in Example 1 between two 5 ml quartz bends. The catalytic bed is reduced for 1 hour at 450° C. and under a hydrogen stream of 2.5 liters per hour. The temperature is then lowered to 240° C. By means of a push syringe, the toluene solution of senecioic acid (18% wt/wt acid/toluene) is injected at a flow rate of 4 ml/h. The gas from the reaction is condensed. After 2 hours of reaction, analysis of the condensate gives the senecioic acid transformation rate (TT) and the real prenal yield.

$$TT = \frac{\text{number of moles of acid present initially} - \text{number of remaining moles of acid}}{\text{number of moles of acid present initially}}$$

$$RR = \frac{\text{number of moles obtained}}{\text{number of moles used}}$$

$$RT = \frac{RR}{TT}$$

At the end of 2 hours of reaction at 240° C., TT=65% and RR=38%.

EXAMPLE 3

Catalysts with a variable Sn/Ru ratio were prepared according to Example 1 for a mass ruthenium content of 0.63% (wt/wt). Reduction of the senecioic acid into prenal took place in accordance with Example 2.

| Catalyst: RuSnB/γAl$_2$O$_3$ Sn/Ru (mole/mole) | TT (%) senecioic acid | RR (%) prenal | RT(%) |
| --- | --- | --- | --- |
| 10 | 11 | 6.2 | 57 |
| 4.2 | 65 | 38 | 59 |
| 2 | 11 | 8.5 | 78.5 |
| 1 | 12 | 7.5 | 62 |

EXAMPLE 4

With a fixed Sn/Ru ratio of 4.2 mole/mole, preparation took place according to Example 1 of catalysts having a variable ruthenium content. The reduction of senecioic acid into prenal was performed in accordance with Example 2.

| % Ru (wt/wt) | TT (%) sonecioic acid | RR (%) prenal | RT (%) |
| --- | --- | --- | --- |
| 0.63 | 65 | 38 | 59 |
| 2 | 43 | 25.5 | 60 |
| 3.15 | 59.5 | 31.5 | 52.5 |

EXAMPLE 5

Different supports were used for preparing catalysts with 0.63% (wt/wt) Ru and Sn/Ru=4.2 (mole/mole) according to Example 1. They were then compared during senecioic acid reduction according to Example 2.

| Support | TT (%) senecioic acid | RR(%) prenal | RT(%) |
| --- | --- | --- | --- |
| γAl$_2$O$_3$ | 65 | 38 | 59 |
| αAl$_2$O$_3$ | 41 | 34 | 83 |
| SiO$_2$ XOA 400 | 16 | 7.5 | 47.5 |
| SiO$_2$ XO 30LS | 30 | 27 | 89.5 |
| Acetylene black | 26.5 | 25 | 96 |
| CECA 3S black | 26 | 12 | 44.5 |

EXAMPLE 6

Senecioic acid reduction is compared on the Ru-Sn-B/γAl$_2$O$_3$ catalyst with 0.63% (wt/wt) Ru and Sn/Ru=4.2 activated for 1 hour under H$_2$, in accordance with Example 2 and at different temperatures before carrying out the reaction at 240° C.

| Activation temperature (°C.) | TT (%) sonecioic acid | RR (%) prenal | RT (%) |
| --- | --- | --- | --- |
| 240 | 87 | 31 | 35 |
| 350 | 60 | 45 | 75 |
| 450 | 69 | 38 | 59 |

EXAMPLE 7

The senecioic acid was diluted to 18% (wt/wt) in 3 different solvents. Comparison took place of the reduction of the acid according to Example 2 on a catalyst having 0.6% Ru and Sn/Ru=4.2 (mole/mole) on γAl$_2$O$_3$, chemically reduced with KBH$_4$ according to Example 1.

| Solvent | TT (%) senecioic acid | RR(%) prenal | RT(%) |
| --- | --- | --- | --- |
| toluene | 81.5 | 50 | 61 |
| DME | 80 | 56.5 | 70.5 |
| DME + H$_2$O | 52 | 36 | 70 |

*H$_2$O added in stoichiometric ratio vith the sonecioic acid.

EXAMPLE 8

The catalysts described can be used for the synthesis of various aldehydes under the conditions of Example 2.

| Acid to be hydrogenated | TT (%) Acid | Sought aldehyde | RR(%) | RT(%) |
| --- | --- | --- | --- | --- |
| 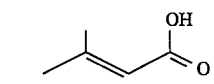 | 65 | 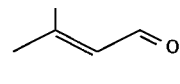 | 38 | 59 |
| 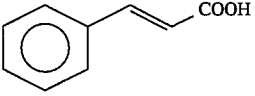 | | 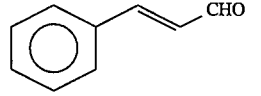 | Qualitative test only | |

-continued

| Acid to be hydrogenated | TT (%) Acid | Sought aldehyde | RR(%) | RT(%) |
|---|---|---|---|---|
| C₆H₅-COOH (benzoic acid) | 76 | C₆H₅-CHO (benzaldehyde) | 58 | 76 |
| (CH₃)₂CHCH₂C(OH)=O (isovaleric acid) | 85.5 | (CH₃)₂CHCH₂CHO (isovaleraldehyde) | 76 | 89 |

EXAMPLE 9

The procedure of Example 2 is employed using an acid solution in dimethoxyethane, so as to obtain:

| Acid | T °C. | TT | RR aldehyde |
|---|---|---|---|
| salicylic acid (2-hydroxybenzoic acid) | 300° C. | 90 | 10% |
| 4-hydroxybenzoic acid | 300° C. | 85 | 50% |

EXAMPLE 10

In a diameter 18 mm tubular glass reaction are placed 2 ml of catalyst obtained in Example 1 replacing the γ alumina by $SiO_2$ XOL 30, between two 5 ml quartz beds. The catalytic bed is reduced for 1 hour at 450° C. under a hydrogen stream of 2.5 liters per hour. The temperature is then dropped to 275° C. Using a push syringe injection then takes placed of the toluenic solution of 3,4-difluorobenzoic acid 10% wt/vol. acid/toluene at a flow rate of 3 ml/h. The gas resulting from the reaction is condensed. Following 2 hours reaction, the analysis of the condensate gives the transformation rate and the real aldehyde yield (RR).

TT=100%

RR=65%.

At 300° C. and replacing $SiO_2$ XOL by $SiO_2$ OX 50 (Degussa), the following yields are obtained:

TT=100%

RR=80%.

EXAMPLE 11

In a diameter 18 ml tubular glass reaction is placed 1 ml of catalyst obtained according to Example 1 between two 5 ml quartz beds. The catalytic bed is reduced for 1 hour at 450° C. under a hydrogen flow of 2 liters per hour. The temperature is then lowered to 300° C. Using a push syringe injection then takes place of the toluenic solution of benzoic anhydride 10% wt/vol. anhydride/toluene at a flow rate of 2 ml/h. The gas from the reaction is condensed. After 6 hours of reaction, analysis of the condensate gives the transformation rate (TT) and the real aldehyde yield (RR).

TT=86%

RR=39%.

EXAMPLE 12

Into a stirred 500 ml reactor are introduced 0.375 g of $RuCl_3$ $xH_2O$ (dissolved beforehand in 40 ml of water). Accompanied by stirring, addition takes place in 30 minutes of 1.5 g of $SnCl_2$, $2H_2O$ dissolved in 150 ml of water. Accompanied by stirring, addition takes place of 25 g of $SiO_2$ OX50 (Degussa). Stirring takes place for 15 minutes and then stirring is stopped and the produced is allowed to stand for 16 hours. At the end of this time, evaporation takes place to dryness by heating at 80° C. under 20 mm of mercury. The residue is then dried under 20 mm of mercury at 40° C. in the oven.

This gives a Ru-Sn/$SiO_2$ catalyst with Sn/Ru=4.0 (mole/mole), i.e. 0.6% Ru (wt/wt).

EXAMPLE 13

In a diameter 18 mm tubular glass reactor is placed 1 ml of catalyst obtained according to Example 12 between two 5 ml quartz beds. The catalytic bed is reduced for 1 hour at 450° C. under a hydrogen flow of 2.0 liters per hour. The temperature is then reduced to 200° C. Using a push syringe, injection then takes place of trifluoroacetic acid under a hydrogen flow of 2.0 liters per hour and at a flow rate of 1 ml per hour. The gases from the reaction are condensed. After 5 hours reaction, analysis of the condensate gives the following results:

TT trifluoroacetic acid=68%

RR monohydrated fluoral=64%.

EXAMPLE 14

In a diameter 18 mm tubular glass reactor is placed 1 ml of catalyst obtained according to Example 12 between two 5 ml quartz beds. The catalytic bed is reduced for 1 hour at 450° C. under a hydrogen flow of 3.0 liters per hour and the temperature is then reduced to 400° C. Using a push syringe, acetic acid is introduced under a hydrogen stream of 3.0 liters per hour and at a flow rate of 1 ml per hour. The gases from the reaction are condensed. After 5 hours reaction, analysis of the condensate by gas chromatography gives the following results:

TT acetic acid=87%

RR acetaldehyde=30%.

EXAMPLE 15

In a diameter 18 mm tubular glass reactor is placed 1 ml of catalyst obtained according to Example 12 between two 5 ml quartz beds. The catalytic bed is reduced for 1 hour at 450° C. under a hydrogen stream of 3.0 liters per hour and the temperature is then lowered to 300° C. Using a push syringe, injection then takes place of a solution of 10% by weight salicylic acid in 1,2-dimethoxyethane under a hydrogen stream of 3.0 liters per hour and at a flow rate of 8 ml per hour. The gases from the reaction are condensed. After 2 hours reaction, analysis of the condensate by gas chromatography gives the following results:

TT salicylic acid=50%

RR salicylic aldehyde=30%

RR phenol=6%.

EXAMPLE 16

Into a three-necked flask equipped with a thermometer, a distillation column, a reflux condenser, a cooler and a separator are introduced salicylic aldehyde (600 mmole) prepared according to the previous example and recovered by distillation and acetic anhydride (1.90 mmole) dissolved in acetic acid (3.47 g).

The product is heated to reflux and sodium acetate (2.1 mmole) dissolved in acetic acid (3.47 g) is introduced. The acetic acid is distilled, whilst maintaining a reflux such that the column head temperature is close to 118° C. After 170 minutes reaction, the coumarin is dosed in the distilling apparatus by gas chromatography, which makes it possible to determine a coumerin yield of 81%.

We claim:

1. A bimetallic catalyst for use in the preparation of aldehydes from acids comprising tin and ruthenium, which catalyst is optionally supported and is free of boron and wherein the tin and ruthenium are present in amounts such that the molar ratio of tin to ruthenium is not less than 2.

2. The bimetallic catalyst according to claim 1 which is supported and which is produced by depositing metallic tin and ruthenium on a support and then reducing the thus obtained contact mass by means of hydrogen.

3. The bimetallic catalyst according to claim 1, wherein the molar ratio of tin:ruthenium is between 2:1 and 10:1 inclusive.

4. The bimetallic catalyst according to claim 3 wherein the molar ratio is between 2:1 and 6:1 inclusive.

5. The bimetallic catalyst according to claim 3 wherein the ruthenium is present in an amount of about 10–50% by weight based on the catalyst.

6. The bimetallic catalyst according to claim 3 wherein the ruthenium is selected from the group consisting of metallic ruthenium, ruthenium (III) chloride, ruthenium (IV) chloride, ruthenium pentafluoride, ruthenium (II) oxide, ruthenium (IV) oxide, ammoniacal ruthenium oxychloride, ruthenium acetate and mixture thereof.

7. The bimetallic catalyst according to claim 3 wherein the ruthenium is introduced as ruthenium (III) chloride.

8. The bimetallic catalyst according to claim 3 wherein the tin is selected from the group consisting of metallic tin, tin oxide, tin chloride, tin nitrate, tin carboxylate, tin alkoxide, a metalorganic compound containing tin which is linked with at least one of a hydrogen atom and an alkyl radical having 1–4 carbon atoms and mixtures thereof.

9. The bimetallic catalyst according to claim 8 wherein the tin is introduced in the form of tin (II) chloride, tin (IV) chloride, tin (II) acetate, tin (II) octoate, tin ethylhexanoate or mixtures thereof.

10. The bimetallic catalyst according to claim 3 where the ruthenium and tin are deposited on a support.

11. The bimetallic catalyst according to claim 10 which support is selected from the group consisting of metal oxides, carbons, acetylene black, and resins.

12. The bimetallic catalyst according to claim 10 wherein the ruthenium is present in an amount of about 0.1–20% by weight based on the catalyst.

13. The bimetallic catalyst according to claim 10 wherein the ruthenium is present in an amount of 0.5–3% by weight based on the catalyst.

* * * * *

UNITED STATES PATENT AND TRADEMARK OFFICE
CERTIFICATE OF CORRECTION

PATENT NO. : 5,476,827
DATED : December 19, 1995
INVENTOR(S) : Rose-Marie FERRERO et al It is certified that error appears in the above-indentified patent and that said Letters Patent is hereby corrected as shown below:

IN THE CLAIMS

In claim 1, col. 17, lines 34-35, please delete "for use in the preparation of aldehydes from acids".

Signed and Sealed this

Third Day of September, 1996

BRUCE LEHMAN

Attest:

Attesting Officer    Commissioner of Patents and Trademarks